United States Patent [19]

Walker

[11] 4,419,120
[45] Dec. 6, 1983

[54] CONTROL OF PRICKLY SIDA, VELVETLEAF, AND SPURRED ANODA WITH FUNGAL PATHOGENS

[75] Inventor: Harrell L. Walker, Stoneville, Miss.

[73] Assignee: The United States of America as represented by the Secretary of Agriculture, Washington, D.C.

[21] Appl. No.: 356,864

[22] Filed: Mar. 10, 1982

[51] Int. Cl.$^3$ ............................................ A01N 63/00
[52] U.S. Cl. ...................................................... 71/79
[58] Field of Search ............................ 71/79; 435/929

[56]  References Cited
U.S. PATENT DOCUMENTS 3,849,104 11/1974 Daniel et al. ............................ 71/65
3,999,973 12/1976 Templeton .............................. 71/79

OTHER PUBLICATIONS

Walker, Weed Science, vol. 29 (1981), pp. 505–507.
Patyka et al. Chem. Abst., vol. 82 (1975) 11995x.

Primary Examiner—Catherine L. Mills
Attorney, Agent, or Firm—M. Howard Silverstein; David McConnell; Raymond C. Von Bodungen

[57]  ABSTRACT

This invention relates to a method for biological control of multiple plant weeds, prickly sida, velvetleaf, and spurred anoda. The control is accomplished using a specific host strain of the fungus *Fusarium lateritium* to produce typical lesions in and kill the multiple weeds. *Fusarium lateritium* is on deposit with the USDA-SEA-AR Southern Weed Science Laboratory in Stoneville, Miss.; the Fusarium Research Center, Pennsylvania State University (Collection No. L-105); and with the Agriculture Research Culture Collection (NRRL), Peoria, Ill., and assigned the #12552.

7 Claims, No Drawings

CONTROL OF PRICKLY SIDA, VELVETLEAF, AND SPURRED ANODA WITH FUNGAL PATHOGENS

BACKGROUND OF THE INVENTION

1. Field of the Invention

The instant invention is a method for the control of undesirable plants by use of plant pathogens.

2. Description of the Prior Art

The merits for using plant pathogens to control weeds in annual crops have been discussed previously for two Colletotrichum spp. (Daniel, et al. U.S. Pat. No. 3,849,104 and Templeton, U.S. Pat. No. 3,999,973). The anthracnose fungus *Colletotrichum gloeosporioides* has been used to control the weed northern jointvetch, and another strain of this fungus has been used to control winged waterprimrose. *Colletotrichum malvarum* has been used to control prickly sida. These three pathogens have been combined to control all three target weeds at once. In other work the fungus *Alternaria macrospora* has been used to control spurred anoda. *Alternaria macrospora,* Weed Science, L. Walker 1981, Vol. 29, pp 505-507.

A major constraint to commercial development of a plant pathogen as a biological herbicide is selectivity. A pathogen that controls only one weed species in one crop does not have the same market potential as a pathogen that controls several important weeds in several crops. In all prior work, no one pathogen has been found that would control two or more important weed species.

Prickly sida is an annual broadleaf herb, that is naturalized from South America. This weed is a pest in soybeans and cotton. Yield reductions occur at low weed densities. Seedlings emerge throughout the growing season, and multiple chemical herbicide applications are necessary to control the weed. This species is a member of the Malvaceae, and is closely related to cotton. The herbicides norflurazon and bentazon are commonly used to control prickly sida in cotton and soybeans, respectively. One plant pahthogen (*Colletotrichum malvarum*) has been tested experimentally for the control of prickly sida, U.S. Pat. No. 3,999,973.

Velvetleaf, a native of Asia, is also closely related to cotton. This species, a broadleaf annual, is a serious weed problem in soybeans, corn, and cotton. Significant crop yield losses occur at low weed densities. Present control methods are limited to cultivation and chemical herbicides. Norflurazon, bentazon, and 2,4-D are commonly used in cotton, soybeans, and corn, respectively.

Spurred anoda is an annual broadleaf species that is native to South America and the Southwestern United States. This weed which is closely related to cotton is a serious pest in cotton and is increasing in importance in soybeans and several other agronomic crops in the Southern United States. Spurred anoda is a strong competitor with crop plants, and even low weed densities, this weed produces significant crop yield losses. Even partial control can be difficult and expensive. Present control methods for spurred anoda are limited to cultivation, and to multiple applications of chemical herbicides. Norflurazon is used for control in cotton, and bentazon is used to control this weed in soybeans. Plants larger than the fifth leaf stage are difficult to control with any of the commonly used herbicides. The fungus *Alternaria macrospora* has been used experimentally to control spurred anoda. *Alternaria macrospora,* Weed Science, L. Walker, 1981, Vol. 29, pp. 505-507.

SUMMARY OF THE INVENTION

The instant invention is a method which was developed to control multiple varities of weeds in agricultural crops. More specifically, the control of prickly sida, velvetleaf, and spurred anoda, three important weeds in agricultural crops. The method consists of inoculation of a field with the fungus *Fusarium lateritium*. This fungus controls all three weed species, but does not harm crop plants. This is an entirely new fungus for the control of these three weeds all at the same time. The process of large scale production, formulation, and application are also new.

DESCRIPTION OF THE PREFERRED EMBODIMENTS

*Fusarium lateritium* Nees ex Fr. is on deposit with the USDA-SEA-AR Southern Weed Science Laboratory in Stoneville, Miss.; and with the Agricultural Research Culture Collection (NRRL) in Peoria, Ill., and has been assigned the following accession number: NRRL #12552. The address of the Agricultural Research Culture Collection (NRRL) is:

A. J. Lyons, Curator, ARS Patent Collection Culture Collection Research NRRC, 1815 N. University St., Peoria, Ill. 61605.

Spores (macroconidia) of this fungus are typically falcate to straight, 3-7 septate, beaked at the apex and have a prominent foot cell. These spores measure $40-75 \times 2.5-5\mu$. Microconidia are absent. Chlamydospores are generally sparse.

*Fusarium lateritium* NRRL #12552 was isolated from stem sections of cankers from diseased spurred anoda plants, were surface sterilized for 5 to 10 min. in 1% (v/v) sodium hypochlorite, rinsed in sterile distilled water, then placed in petri dishes containing potato dextrose agar (PDA) with 125 mg/l streptomycin sulfate and 75 mg/l chloramphenicol. Cultures were incubated at 25° C. with 12 h diurnal light. The light was supplied by two 15-W cool-white fluorescent lamps that were suspended 45 cm above the cultures.

The pathogen was grown on V-8 juice agar supplemented with 1.3 g/L of L-proline. A sterile distilled water rinse was used to harvest the spores from 7 to 10 day old cultures, and the spore concentrations were determined with a hemacytometer. The fungus was maintained on PDA at 25° C., and preserved in screw capped culture tubes of twice autoclaved sandy loam. The soil cultures were stored at room temperature (23°-26° C.) and at 4° C.

Plant species included in the host range studies for the Fusarium sp. are listed in Table I. These seedlings were grown in a commercial potting mix in peat strips that contained 12 plants each and were fertilized weekly with a water soluble fertilizer. Greenhouse temperatures ranged from 28° to 32° C. with 50 to 80% relative humidity. The day length was approximately 12 h with 1650 $\mu E \cdot m^{-2} \cdot s^{-1}$ photosynthetically active radiation at noonday.

Except where noted, the plants used in these studies were in the cotyledon to first leaf stage of growth at the time of inoculation. The plants were sprayed to wetness using an atomizer connected to a portable air pump. Inoculation mixtures contained 0.02% (v/v) surfactant, nonoxynol (9 to 10 POE) 1a-(p-nonyl-phenyl)-w-hydroxypoly (oxyethylene) in distilled water and $1 \times 10^5$ Fusarium spores/ml. Control plants were sprayed with water and 0.02% surfactant only. All plants were placed in dew chambers for 19 h at 25° C. The plants were then moved to greenhouse benches and evaluated daily for 14 days. All tests were repeated on at least two dates and 12 plants were used for each treatment or control in each test.

The Fusarium isolate grew well and sporulated profusely on the modified V-8 juice agar. Cultures grown on PDA (pH 5.8) produced a blue pigment and cultures grown on the modified V-8 juice agar (pH 6.9), produced a blue-green pigment. Both fungi were readily recovered from the soil cultures after storage for as long as 18 months.

Spurred anoda, prickly sida, velvetleaf, okra, Venice mallow, and hollyhock were susceptible to *Fusarium lateritium* (Table I). Disease symptoms first appeared 24 to 48 hours after inoculation as cotyledonary and leaf lesions. These tan to dark brown lesions, initially pinpoint to 1 mm in diameter, enlarged rapidly and often induced defoliation of the cotyledons and inoculated leaves within 72 hours after inoculation. Stem lesions often occurred at the base of infected petioles. Oblong, tan stem lesions, up to 2 mm in length, were apparent 48 to 72 hours after inoculation. These lesions became dark brown to black after 3 to 5 days and enlarged with time to become sunken in appearance. These lesions girdled the stems of 50 to 100% of the susceptible plant species within 2 weeks. Of the susceptible species, prickly sida and velvetleaf seedlings appeared to be most severely affected by the pathogen; whereas, spurred anoda seedlings were the most tolerant. Corn, cotton, soybeans, and 13 other crop and weed species in six families were resistant to the pathogen (Table I).

A search of the literature revealed that this pathogen had not been previously reported on these weeds.

EXAMPLE 1

Large scale production and granular formulation

A laboratory fermenter was used to culture mycelia of the fungus in 10-L quantities of V-8[3] juice medium that had been modified by deletion of the agar and by the addition of 30 g/L sucrose. Conidia for inoculum for the liquid medium were aseptically harvested in sterile distilled water from 5- to 7-day-old cultures grown in petri plates of V-8 juice agar that were incubated at 25° C. with 12 hour diurnal light. Light was provided by two 20-W, cool-white fluorescent lamps suspended 45 cm above the cultures. Approximately 5 ml of the conidia/water suspension was aseptically injected into each fermenter vessel. A silicon-based antifoam agent was added to a final concentration of 0.02% (v/v).

The cultures in the fermenter vessels were maintained at 25±1 C. with vigorous agitation and aeration. After 48 to 72 hours, the mycelia were harvested and comminuted. Blended mycelia from each 10-L culture were mixed with approximately 1000 g of horticultural vermiculite divided among 8 to 10 aluminum foil-lined plastic pans (41 by 27 by 5.5 cm). The pans of freshly poured vermiculite-mycelia mixture were covered with a clear polyethylene film to produce granular formulations containing abundant spores of *F. lateritium* NRRL #12552. This covering prevented rapid drying and permitted the 24- to 48-hour incubation times necessary for optimum spore production. These granular preparations contained $6 \times 10^6$ macroconidia/g of the air-dried vermiculite preparation. These pans of vermiculite and mycelia were exposed to 7 hour diurnal light that was provided by two 40-W, cool-white fluorescent lamps. Recent studies have shown that the light requirement for sporulation can be provided by a single 20- to 30-min exposure to direct sunlight. After 24 hours, the surfaces of the vermiculite particles were covered with spores. The formulation of vermiculite-mycelia-spores was air-dried in an incubator at 35° C. for 24 to 48 hours, then sieved, packaged in plastic bags, and stored at 4° C. Spore counts were estimated with a hemacytometer after the spores were eluted from a known weight of the granular preparation into water. For mycelia yield determinations, the mycelia were collected onto window screen, washed with distilled water, and dried to constant weight at 75° C.

TABLE I

REACTION OF VARIOUS PLANT SPECIES TO *FUSARIUM LATERITIUM* IN THE GREENHOUSE[1]

| Amaranthaceae | |
| --- | --- |
| Pigweed (*Amaranthus* sp.) | R |
| Compositae | |
| Cocklebur (*Xanthium pensylvanicum* Wallr.) | R |
| Aster (*Aster* sp.) | R |
| Gramineae | |
| Corn (*Zea mays* L.) | |
| 'Trucker's Favorite' | R |
| 'XL 394' | R |
| Barnyardgrass [*Echinochloa crus-galli* (L.) Beauv.] | R |
| Grain sorghum [*Sorghum bicolor* (L.) Moench] | |
| 'Texas C 424' | R |
| Johnsongrass [*Sorghum halepense* (L.) Pers.] | R |
| Wheat (*Triticum aestivum* L.) | |
| 'Coker 68-15' | R |
| Oats (*Avena sativa* L.) | R |
| Leguminosae | |
| Crotalaria (*Crotalaria spectabilis* Roth) | R |
| Hemp sesbania [*Sesbania exaltata* (Raf.) Cory] | R |
| Northern jointvetch [*Aeschynomene virginica* (L.) B.S.P.] | R |
| Soybean [*Glycine max* (L.) Merr.] | |
| 'Forrest' | R |
| 'Lee' | R |
| Sicklepod (*Cassia obtusifolia* L.) | R |
| Malvaceae | |
| Cotton (*Gossypium hirsutum* L.) | |
| 'Camd-E' | R |
| 'Camd-S' | R |
| 'Deltapine 61' | R |
| 'Stoneville 213' | R |
| Cotton (*Gossypium barbadense* L.) | |
| 'Pima S-5' | R |
| Hollyhock [*Althaea rosea* (L.) Cav.] | S |
| Okra [*Abelmoschus esculentus* (L.) Moench] | |
| 'Clemson Spineless' | S |
| Prickly sida (*Sida spinosa* L.) | S |
| Spurred anoda [*Anoda cristata* (L.) Schlecht.] | S |
| Velvetleaf (*Abutilon theophrasti* Medic.) | S |
| Venice mallow (*Hibiscus trionum* L.) | S |
| Solanaceae | |
| Tomato (*Lycopersicon esculentum* Mill.) | |
| 'Big Boy' | R |
| 'Heinz' | R |
| 'Rutgers' | R |

[1]The plants were inoculated with foliar applications of spray mixtures that contained $2 \times 10^5$ macroconidia/ml and surfactant. Plants were observed 4 weeks after inoculation.
R = resistant, S = susceptible The method described permits the granular formulation of *F. lateritium*, NRRL #12552. Greenhouse and field studies indicate that this type of formulation, when applied to the soil either preemergence or postemergence, can be effective for initiating disease on spurred anoda, prickly sida, and velvetleaf seedlings. A formulation of *F. lateritium* with residual activity that can be applied at the time of planting for spurred anoda control could enhance the effectiveness of the pathogen by concentrating the inoculum in a band on top of the seed furrow. This would help to ensure that the pathogen will infect weed seedlings as they emerge and will reduce or eliminate the multiple applications that would be necessary for foliar applications of the pathogen.

EXAMPLE 2

Control of prickly sida and velvetleaf in cotton

Greenhouse studies for the feasibility of utilizing the granular formulation as inoculum were conducted in flats (52 by 25 by 6.5 cm) of pasteurized sandy loam. To study the feasibility of utilizing this type of formulation for preemergence applications, seeds of prickly sida and velvetleaf plus 'Stoneville 213' cotton, and cotton only, were seeded in flats of pasteurized soil. Each flat had a total of 24 cotton seeds arranged in one furrow along each side of the flat. Eighty seeds for both prickly sida and velvetleaf were broadcast in each flat. The seeds were previously scarified 15 min in concentrated sulfuric acid, rinsed in tap water, and air-dried. The seeds were then covered with a small amount of additional soil. Fifteen grams (1155 kg/ha) of the *F. lateritium* NRRL #12552-vermiculite formulation, or 15 g of blank vermiculite, was spread evenly on the soil surface of each flat.

Flats were placed on benches in a temprature-controlled greenhouse maintained at 28° to 32° C. with 40 to 60% relative humidity. The day length was approximately 12 h with 1650 $\mu E \cdot m^{-2} \cdot s^{-1}$ at noonday. Flats were watered from the bootom by subirrigation as needed. Dew chambers were used to provide moisture for spore germination. Seven and eight days after emergence of the cotton, prickly sida, and velvetleaf seedlings, all plants received two 18-h dew periods at 25° C. All greenhouse studies were replicated three to five times with one flat per replication and were repeated on three different dates. A randomized block design was used. Seedlings were harvested 4 weeks after seeding. Mean differences were determined by Duncan's multiple range test at the 5% confidence level. In greenhouse tests, the fungus controlled 90 to 100% of prickly sida and velvetleaf seedling after four weeks when applied preemergence, Table II.

TABLE II

REACTION OF COTTON, PRICKLY SIDA AND VELVETLEAF TO A PREEMERGENCE APPLICATION OF *FUSARIUM LATERITIUM* IN THE GREENHOUSE[1]

| | No. of plants alive after 4 weeks | | |
|---|---|---|---|
| | Cotton | Prickly sida | Velvetleaf |
| Control[2] | 21 | 82 | 50 |
| Treated[3] | 21 | 3 | 1 |

[1]Flats of Bosket silt loam. Treatments were replicated and randomized.
[2]Each flat received 15 g blank vermiculite.
[3]each flat received 15 g of *F. lateritium/vermiculite* formulation ($6 \times 10^6$ macroconidia/g).

EXAMPLE 3

Combination of pathogens

Spurred anoda plants in the second to third leaf stage of growth were used to study the disease symptoms produced by combining *A. macrospora* and the Fusarium sp. The pathogens were applied alone and in combination. The spore concentrations in spray mixtures were $2.5 \times 10^4$ spores/ml for each pathogen. After inoculation, the plants were given an 18 h dew period, then moved to the greenhouse.

The spurred anoda plants inoculated with *A. macrospora* developed multiple stems and leaf lesions. About 50% of the inoculated leaves were defoliated within 4 to 6 days after inoculation. The tan stem lesions were oblong and 1 to 2 mm in length and were first apparent 48 to 72 h after inoculation. Most stem lesions were superficial, and could be removed with the epidermis.

The spurred anoda plants inoculated with the Fusarium only developed fewer leaf and stem lesions then the plants that were inoculated with *A. macrospora* only, and these lesions were generally slower to develop. No appreciable defoliation of inoculated leaves occurred. The stem lesions that developed were dark brown and penetrated into the conductive tissues. Within 10 to 14 days after inoculation, the stems of about 25% of the plants were girdled by cankers.

Spurred anoda plants that were inoculated with *A. macrospora* plus the Fusarium sp. exhibited severe disease symptoms. Multiple stem lesions developed within 48 to 72 h after inoculation. These dark brown to black lesions rapidly enlarged to form 1- to 4-cm long sunken cankers that girdled the stems in multiple locations. The symptoms progressed and 75 to 100% mortality occured within 2 weeks after inoculation. These symptoms closely resembled those exhibited by the field collected spurred anoda plants. Combinations of *F. lateritium* and *A. macrospora* could be more effective control of spurred anoda, particularly older plants, than can be achieved by *A. macrospora* alone.

EXAMPLE 4

Control of spurred anoda and prickly sida in the field

In the summer and fall of 1979 and 1980, a naturally occurring disease occurred at Stoneville, Miss., in dense stands of spurred anoda plants that were cultivated to supply seeds for weed control research. Disease symptoms included stem cankers that girdled the stems. Many plants were stunted or killed and seed production was greatly reduced. Many of the severely damaged plants were 1-m or more in height and had several secondary branches. *F. lateritium* NRRL #12552 was isolated from these plants.

In the spring of 1980, an epidemic occurred in a stand of prickly sida plants that were growing in the same field as the diseased spurred anoda plants. Most of these plants were in the cotyledonary to fourth leaf stage of growth. On May 21 the prickly sida plants in 10 randomly selected 1-$m^2$ plots were counted and evaluated for disease symptoms. The stand consisted of an average of 108 prickly sida seedlings per $m^2$. An average of 66% of these plants were dead and 37% of the remaining live plants exhibited disease symptoms. After two weeks the number of live seedlings was reduced to 28/$m^2$, and 87% of these remaining plants exhibited disease symptoms. The plants that did not exhibit disease symptoms were seedlings in the cotyledonary stage of growth that had emerged within the previous 2 or 3 days. The disease symptoms included cankers that girdled stems and roots and induced wilting. These lesions were dark brown to black, sunken, and penetrated to the conductive tissues. A Fusarium sp. was isolated from the diseased prickly sida plants, and spore morphology, culture characteristics, and host range studies indicated this to be the same pathogen that was previously isolated from disease spurred anoda plants.

The foilar pathogen can be formulated and applied as a spray (wettable powder) or as granules that consist of the fungus and a carrier such as vermiculite, corn cob grits, or clay. Preemergence or postemergence applications of granules can be used. The granular formulation of a foilar pathogen for soil applications for preemergence weed control is not easily recognizable because soil inhabiting organisms compete with the pathogen. The satisfactory performance of this fungus for preemergence weed control was extremely difficult to identify because soil-inhibiting oraganisms compete with the pathogen. The satisfactory performance of this fungus for preemergence weed control is determined by the method of formulation. All the prior art concerning weed control with plant pathogens have involved pathogens that controlled only one weed species. *Fusarium lateritium* controls multiple weed species without damage to crop plants. Since the target weeds affected by this pathogen are so close to the agricultural crop to be protected it was even more difficult to develop the instant invention.

In no other prior art have two weed pathogens been demonstrated to produce enhanced control of a single weed species. Mixtures of *Alternaria macrospora* and *Fusarium lateritium* produce a disease complex that is effective for the control of spurred anoda. This interaction is difficult to develop because it was not heretofore known to exist, and because *F. lateritium* produces an antifungal inhibitor that retards the growth of *A. macrospora* in laboratory cultures. Therefore, this combination represents new art.

The *F. lateritium* was first discovered as part of a disease complex that included *A. macropora*. Initial isolation of *F. lateritium* was impaired by the presence of the *A. macrospora*. *A macrospora* is also a pathogen to spurred anoda, and this fungus grew much faster on the acidified growth media used in initial attmepts. This difficulty was overcome by using growth media containing the antibiotics, and by varying the pH of the growth media. A pH of 5.0 was favorable for isolation of *F. lateritium*, while a pH of 4.5 was favorable for isolation of *A. macrospora*.

Spores (macroconidia) of the *F. lateritium* are not produced in submerged liquid culture. These spores are produced in petri dishes, but this procedure is impractical for large scale production. This difficulty was overcome by a method for large scale production that represents new art.

I claim:

1. A method for controlling multiple plant weeds of prickly sida, velvetleaf, and spurred anoda, comprising infesting agricultural fields with an effective amount of the fungus *Fusarium lateritium* to infect and produce typical lesions in and kill said multiple weeds.

2. The method of claim 1 wherein the fungus *Fusarium lateritium* is NRRL #12552.

3. The method of claim 1 wherein the fungus *Fusarium lateritium* is applied to the agricultural fields as a spray or wettable powder.

4. The method of claim 1 wherein the fungus *Fusarium lateritium* is applied to the agricultural field as granules that consist of the fungus and a carrier such as vermiculite, corn cob grits, or clay.

5. A method for controlling spurred anoda comprising infesting agricultural fields with an effective amount of the fungus *A. macrospora* and *Fusarium lateritium*, NRRL #12552 to infest and kill spurred anoda.

6. The method of claim 5 wherein the combination fungus *A. macrospora* and *Fusarium lateritium*, NRRL #12552 is applied to the agricultural fields as a spray or wettable powder.

7. The method of claim 5 wherein the combination fungus *A. macrospora* and *Fusarium lateritium*, NRRL #12552 is applied to the agricultural fields as granules that consist of the fungus and a carrier such as vermiculite, corn cob grits, or clay.

* * * * *